United States Patent [19]

Kovar et al.

[11] 4,001,268
[45] Jan. 4, 1977

[54] SUBSTITUTED PHENYL-BENZIMIDAZO COMPOUNDS

[75] Inventors: Robert F. Kovar, Dayton; Fred E. Arnold, Centerville, both of Ohio

[73] Assignee: The United States of America as represented by the Secretary of the Air Force, Washington, D.C.

[22] Filed: July 18, 1975

[21] Appl. No.: 597,060

Related U.S. Application Data

[63] Continuation-in-part of Ser. No. 495,471, Aug. 7, 1974, abandoned.

[52] U.S. Cl. .......................... 260/309.2; 260/78 R; 260/78 A; 260/78 TF
[51] Int. Cl.$^2$ ..................................... C07D 235/18
[58] Field of Search ............................... 260/309.2

[56] References Cited

UNITED STATES PATENTS 2,985,661  5/1961  Hein et al. ..................... 260/309.2

FOREIGN PATENTS OR APPLICATIONS 760,694  11/1956  United Kingdom ............ 260/309.2

OTHER PUBLICATIONS

Arient et al., Collect. Czech. Chem. Comm. 1965, vol. 30, pp. 1913–1922.
Jurasek et al., Collect. Czech. Chem. Comm. 1969, vol. 34, pp. 572–581.

*Primary Examiner*—Natalie Trousoe
*Attorney, Agent, or Firm*—Joseph E. Rusz; Cedric H. Kuhn

[57] ABSTRACT

Substituted phenyl-benzimidazo compounds are disclosed in which the phenyl group which is attached to the two position of the imidazo ring contains a carboxylic acid group, or derivatives thereof, para to the point of imidazo attachment. The benzimidazo is substituted in the 5,6 positions with amino groups or derivatives thereof. The compounds are particularly useful as AB-monomers in the preparation of poly [(2,6-imidazobenzimidazo)1,4-phenylene].

3 Claims, No Drawings

SUBSTITUTED PHENYL-BENZIMIDAZO COMPOUNDS

RIGHTS OF THE GOVERNMENT

The invention described herein may be manufactured and used by or for the Government of the United States for all governmental purposes without the payment of any royalty.

This application is a continuation-in-part of pending application Ser. No. 495,471, filed on Aug. 7, 1974, and now abandoned.

FIELD OF THE INVENTION

This invention relates to substituted phenylbenzimidazo compounds and to a process for their preparation. In one aspect it relates to a process for preparing poly[(2,6-imidazobenzimidazo)-1,4-phenylene].

BACKGROUND OF THE INVENTION

An all para-oriented polybenzimidazole is a desirable product because it has the potential of possessing outstanding physical properties. In the preparation of such polymers, the conventional practice is to condense two monomers, e.g., a tetraamine and a tetraacid. However, the polymers prepared by the prior art methods are not entirely satisfactory because of their low molecular weight.

It is an object of this invention, therefore, to provide AB-monomers which can be used in preparing a high molecular weight, all para-oriented polybenzimidazole.

Another object of the invention is to provide an intermediate for use in preparing the AB-monomers.

A further object of the invention is to provide a process for synthesizing substituted phenyl-benzimidazo compounds.

Still another object of the invention is to provide a process for preparing poly[(2,6-imidazobenzimidazo)1,4-phenylene].

Other objects and advantages of the invention will become apparent to those skilled in the art upon consideration of the accompanying disclosure.

SUMMARY OF THE INVENTION

The present invention resides in a substituted phenyl-benzimidazo compound having the following structural formula:

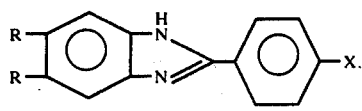

wherein R is $-NO_2$, $-NH_2$, $-NH_3Cl$, or $-NHSO_2R'$ and X is

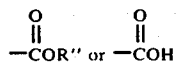

with R' and R" being an aryl, alkyl or cycloalkyl radical.

The AB-monomers of this invention are those compounds according to Formula I in which R is $NH_2$, $NH_3Cl$ or $NHSO_2R'$ and X is as indicated. When preparing monomers in which R is an amino and aminohydrochloride group, initially an intermediate is synthesized in which R is nitro. This synthesis is carried out by condensing 1,2-diamino-4,5-dinitrobenzene with a monochloride terester which is the source of the X group. Basic hydrolysis of the intermediate followed by catalytic reduction in a methanol-hydrochloric acid medium provides a monomer in which R is aminohydrochloride and X is carboxylic acid. Alternatively, omission of the hydrolysis step and catalytic reduction of the intermediate in an acid media gives an AB-monomer in which R is an aminohydrochloride and X is an ester. Treatment of the monomer with an organic base, such as pyridine, gives a monomer in which R is amino and X is an ester group.

The reactions described in the preceding paragraph are illustrated by the following equations:

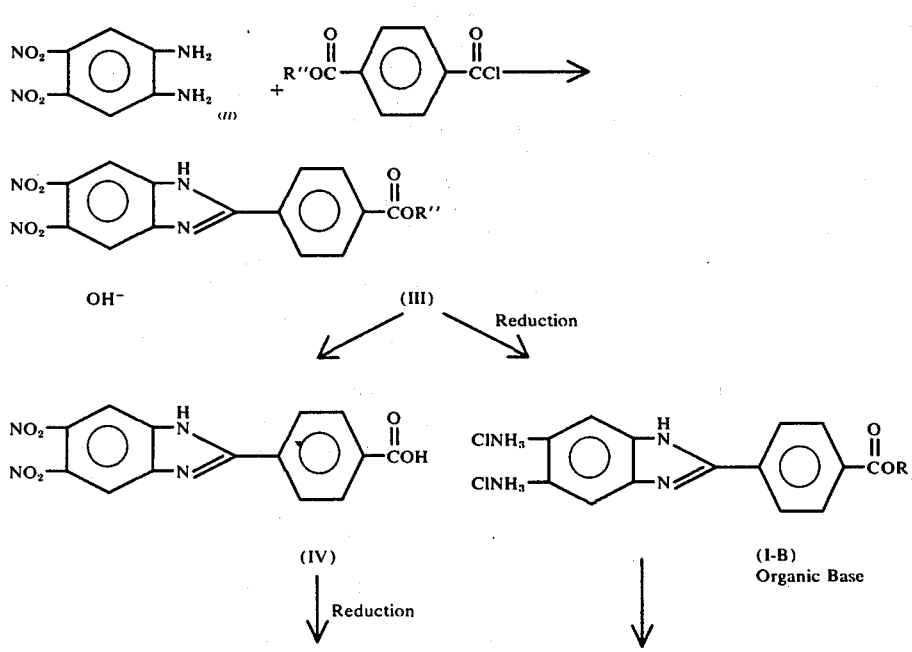

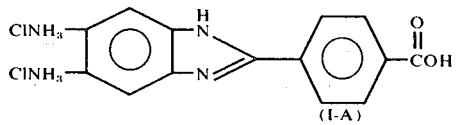
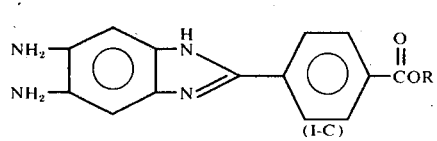

Examples of monochloride teresters that can be used include the monoacid chlorides of methylterphthalate, ethylterphthalate, propylterphthalate, butylterphthalate, cyclopropylterphthalate, cyclopentylterphthalate, cyclohexylterphthalate, cycloheptylterphthalate, tolylterphthalate, xylylterphthalate, phenylterphthalate, biphenylterphthalate, naphthylterphthalate, and the like. The monochloride terester, as indicated hereinabove, is the source of the X group which is an ester group

or, if desired, carboxylic acid when the ester group is hydrolyzed. Examples of R'' radicals corresponding to the aforementioned examples of teresters are methyl, ethyl, propyl, butyl, cyclopropyl, cyclopentyl, cyclohexyl, cycloheptyl, tolyl, xylyl, phenyl, biphenyl, naphthyl, and the like.

In the condensation reaction represented by equation II, the mole ratio of the monochloride terester to 1,2-diamino-4,5-dinitrobenzene is generally about 3 to 1. The reaction is conducted in an inert solvent, such as dichlorobenzene, under reflux conditions for a period of about 1 to 3 hours. At the end of this period, the reaction mixture is cooled, thereby precipitating the dinitrobenzimidazole product (III). The precipitated product is then purified, e.g., by washing with a hydrocarbon, such as benzene, drying, and recrystallization from solution.

In one embodiment the product of the condensation reaction (III) is hydrolyzed by mixing it with an aqueous solution of an alkali metal hydroxide. In this basic hydrolysis, the mol ratio of hydroxide to the dinitrobenzimidazole (III) is usually about 3 to 1. After heating this mixture under an inert gas, such as nitrogen, at a temperature ranging from about 80° to 100° C for a period of about 5 to 10 hours, the solution is acidified, e.g., with hydrochloric acid, thereby producing the dinitro-acid (IV) as a precipitate. After recovery of the precipitate, as by filtration, it is purified by washing with water, drying, and recrystallization from solution. The dinitro-acid product is then catalytically reduced by dissolving it in an alcohol, such as methanol, and adding to the resulting solution a supported palladium catalyst and concentrated hydrochloric acid. This mixture is then pressurized with hydrogen at room temperature over a period of about 6 to 12 hours. After this period a solid material is recovered by filtering the solution and evaporating the filtrate under a vacuum. The solid material is then dissolved in boiling methanol after which the filtered solution is added to concentrated hydrochloric acid. Removal of the methanol from the solution by vacuum distillation followed by cooling yields product (I-A) in which R is aminohydrochloride and X is carboxylic acid, i.e., 2-[p-carboxyphenyl]-5,6-diaminobenzimidazole.

In another embodiment the hydrolysis step as described above is omitted and the product of the condensation reaction (III) is catalytically reduced. The reduction reaction is conducted in the manner described hereinbefore, thereby producing product (I-B) in which R is aminohydrochloride and X is an ester. By treating product (I-B) with an organic base, such as pyridine, product (I-C) is obtained in which R is amino and X is an ester.

When preparing AB-monomers represented by Formula I in which R is NHSO₂R' and X is as indicated, the condensation reaction involved is represented by the following equation:

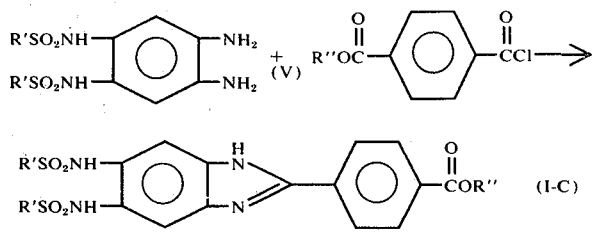

The AB-monomer represented by Formula I-C can be converted to the monomers in which X is carboxylic acid by mixing it with an aqueous solution of an alkali metal hydroxide. The ester group of product (I-C) is thereby hydrolyzed to a carboxylic acid group to give product (I-D) as shown by the following formula:

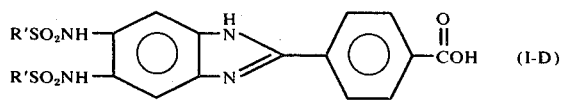

In the above formulas, R' and R'' are as indicated hereinbefore.

Typical sulfonamide derivative groups represented by R'SO₂NH are those in which R' is phenyl, tolyl, xylyl, naphthyl, diphenyl, methylnaphthyl, benzyl, chlorophenyl, bromophenyl, iodophenyl, fluorophenyl, chloronaphthyl, chlorodiphenyl, methyl, ethyl, propyl, amyl, oxtyl, decyl, dodecyl, octadecyl, cyclohexyl, cycloheptyl, methylcyclohexyl, ethylcycloheptyl, and the like. While the sulfonamide derivative groups can be introduced by any convenient means, it is preferably attached by reaction of the amino groups with an appropriate sulfonyl chloride, such as toluene sulfonyl chloride, benzene sulfonyl chloride, xylyl sulfonyl chloride, naphthyl sulfonyl chloride, methyl sulfonyl chloride, propyl sulfonyl chloride, cyclohexyl sulfonyl chloride, and the like. For a more complete discussion of the preparation of the 1,2-disulfonyl derivatives of 1,2,4,5-tetraaminobenzene, U.S. Pat. No. 3,702,326 may be referred to. The disclosure of this patent, which is concerned with these compounds, is incorporated herein by reference.

In the condensation reaction represented by equation (V), the mol ratio of the monochloride terester to the 1,2-disulfonyl of 1,2,4,5-tetraaminobenzene is usually about 3:1. The reaction is carried out under reflux condition in an inert solvent, such as dichlorobenzene, for a period of about 1 to 3 hours. After distilling off a portion of the solvent, a non-solvent, for the product, such as heptane, is added in order to precipitate product (I-C). The product is then recovered, e.g., by filtration, washed with a saturated hydrocarbon, such as hexane, and then air-dried. Further purification is carried out by reprecipitating the product from solution followed by recrystallization from an alcohol, such as methanol.

A more complete understanding of the invention can be obtained by referring to the following illustrative examples which are not intended, however, to be unduly limitative of the invention.

EXAMPLE I a.
2-[p-Carbomethoxyphenyl-]-5,6-dinitrobenzimidazole

To a solution containing 10 g (45.8 mmole) of p-chlorocarbonylmethylbenzoate dissolved in 100 ml of dichlorobenzene was added 3.0 g (15.3 mmole) of 1,2-diamino-4,5-dinitrobenzene. After heating the resulting mixture to reflux under nitrogen (frothing), it was maintained at that temperature for 2 hours. The solution was then allowed to cool in ice for one hour, and the precipitate that formed was filtered by suction, washed with benzene and air-dried. Recrystallization from tetrahydrofuran (THF)-n-propanol by distillation to a small volume in vacuo yielded 3.2 g (62%) of 2-[p-carbomethoxyphenyl]-5,6-dinitrobenzimidazole as light yellow needles, m.p. 239°–240°.

Calc for $C_{14}H_{10}N_3O_5$ (weight %): C,52.65; H,2.92; Found: N,16.37; O,28.05. Found: C,51.78; H,3.13; N,15.66.

Mol Wt. (Calculated) = 342.19
Mol wt (Mass spectrum) =342 b. 2-[p-Carboxyphenyl]-4,5-dinitrobenzimidazole

To a solution containing 4.8 g (87.6 mmole) of KOH dissolved in 200 ml of water was added 10 g (29.2 mmole) of 2-[p-carbomethoxyphenyl]-5,6-dinitrobenzimidazole (as prepared in (a) above). The resulting mixture was heated at 90° C under nitrogen for 8 hours, at which time it was allowed to cool to room temperature. The solution was then slowly acidified with 50% HCl, liberating the dinitro-acid as a light-tan precipitate. The product was collected by filtration, washed with several portions of distilled water and air-dried. Recrystallization from THF-heptane afforded golden platelets, m.p.—dec. above 350° C.

Calc'd for $C_{14}H_8N_4O_6$: C,51.23; H,2.46; N,17.07; O,29.25. Found: C,51.01; H,2.59; N,17.15.

EXAMPLE II

2-[p-Carboxyphenyl]-5,6-diaminobenzimidazole hydrochloride

A solution of 5 g (16.7 mmole) of 2-[p-carboxyphenyl]-5,6-dinitrobenzimidazole (as prepared in Example I) in 200 ml of methanol at 0° C was thoroughly purged with nitrogen. To this was added 500 mg of 10% palladium on charcoal, and 30 ml of concentrated HCl. The hydrogenation flask was then pressurized with 55 lbs/in² of hydrogen, and the flask was shaken at room temperature for 8 hours. After the reaction period had elapsed, the solution was filtered by suction, and the filtrate evaporated to dryness in vacuo. The residual yellow solid was redissolved in a minimum amount of boiling methanol (which contained a trace of HCl), and the filtered solution added to 50 ml of concentrated HCl. Removal of the methanol from the solution in vacuo and subsequent cooling in ice yielded 4.2 g (82%) of 2-[p-carboxyphenyl]-5,6-diaminobenzimidazole hydrochloride as fluffy yellow needles.

Calc'd for $C_{14}H_{12}N_4O_2 \cdot HCl$: C,55.15; H,4.30; N,18.39; O,10.50; Cl, 11.63 M.W. 304.739. Found: C,54.82; H,4.33; N,18.77; Cl, 12.01.

EXAMPLE III

Polymerization of 2-[p-carboxyphenyl]-5,6-diaminobenzimidazole hydrochloride

A polymerization flask equipped with nitrogen inlet and outlet tubes and mechanical stirrer was thoroughly flamed and purged with nitrogen. To this was added 50 g of polyphosphoric acid, and the viscous material was stirred at 150° C under nitrogen for 3 hours. The flask was then cooled in ice, opened, and 2 g (6.56 mmole) of 2-[p-carboxyphenyl]-5,6-diaminobenzimidazole hydrochloride was added. The flask was closed, and the resulting suspension stirred at 90° C for 8 hours under nitrogen to decompose the hydrochloride salt. At that point, a clear, brown solution remained. The temperature of the heating bath was then slowly raised over a period of 3 hours to a maximum of 200° C, and was maintained at that level for 8 hours. During that time, a blue opalescence became evident in the reaction solution, which is characteristic of solutions of this polymer in acidic solvents. The polymer solution was precipitated into a large volume of methanol, and then washed with several portions of methanol. The precipitated polymer was stirred with one liter of 10% ammonium hydroxide solution, then rinsed with several portions of distilled water, and finally freeze-dried. The fluffy yellow polymer thus obtained was soluble in methanesulfonic acid, exhibiting an inherent viscosity in that solvent of 1.3 dl/g (0.35 g/dl).

Calc'd for $(C_{14}H_8N_4)_n$: C,72.40; H,3.47; N,24.1. Found: C,70.56; H,3.28; N,22.66.

EXAMPLE IV

2-[p-Carbophenoxyphenyl]-5,6-dinitrobenzimidazole

To a solution containing 10 g (38.4 mmole) of p-chlorocarbonylphenylbenzoate dissolved in 100 ml of dichlorobenzene was added 2.53 g (12.8 mmole) of 1,2-diamino-4,5-dinitrobenzene. After heating the resulting mixture under nitrogen to reflux (frothing), it was maintained at that temperature for 2 hours. The solution was then allowed to cool in ice for one hour, and the precipitate that formed was filtered by suction, washed with benzene, and air-dried. The crude product was chromatographed on a 2×18 inch dry column of silica gel. Elution with methylene chloride removed traces of impurities, while further elution of the column with 20/1 methylene chloride-THF slowly removed a broad band of the desired product, leaving a third band of side-product on the column. After all of the second band had been removed from the column, the solvent was removed in vacuo leaving a pale yellow residue. Recrystallization from THF-n-propanol yielded 3.0 g (58%) of 2-[p-carbophenoxyphenyl]-5,6-dinitrobenzimidazole as pale yellow needles, m.p. 239°–240°.

Calc'd for $C_{20}H_{12}N_4O_6$: C,59.41; H,2.99; N,13.85; O,23.74. Found: C,60.01; H,3.14; H,12.73.

EXAMPLE V

2-[p-Carbophenoxyphenyl]-5,6-diaminobenzimidazole dihydrochloride

A solution containing 5 g (12.4 mmole) of 2-[p-carbophenoxyphenyl]-5,6-dinitrobenzimidazole (as prepared in Example IV) dissolved in 100 ml of methanol was thoroughly purged with nitrogen at 0° C. To this was added 200 mg of 10% palladium on charcoal and 20 ml of concentrated HCl. The flask was pressurized with 55 lbs/in$^2$ of hydrogen, and was shaken at room temperature for 8 hours. At that time, the contents of the flask were filtered, and the filtrate evaporated to dryness in vacuo, yielding 5.5 g (95%) of 2-[p-carbophenoxyphenyl]-5,6-diaminobenzimidazole dihydrochloride as a yellow powder.

Calc'd for $C_{20}H_{16}N_4O_2 \cdot 2$ HCl: C,57.57; H,4.35; N,13.43; O,7.67; Cl, 16.99. Found: C,57.13; H,4.27; N,12.95; Cl, 16.44.

EXAMPLE VI

Polymerization of 2-[p-Carbophenoxyphenyl]-5,6-Diaminobenzimidazole dihydrochloride A polymerization flask equipped with nitrogen inlet and outlet tubes and mechanical stirrer was thoroughly flamed and purged with nitrogen. To this was added 50 g of polyphosphoric acid, and the viscous material stirred at 150° C under nitrogen for 3 hours. The flask was then cooled in ice, opened, and 2.0 g (4.8 mmole) of 2-[p-carbophenoxyphenyl]-5,6-diaminobenzimidazole dihydrochloride added. The flask was closed, and the resulting suspension stirred at 90° C for 8 hours under nitrogen to decompose the hydrochloride salt. At that point, a clear, brown solution remained. The temperature of the heating bath was then slowly raised over a period of 3 hours to a maximum of 200° C and was maintained at that level for 8 hours. During that time, a blue opalescence became evident in the reaction solution, which is characteristic of solutions of the benzimidazole polymer in acidic solvents. The polymer solution was precipitated into a large volume of methanol, and then washed with several portions of methanol. The precipitated polymer was stirred with 1 liter of 10% ammonium hydroxide solution, then rinsed with several portions of distilled water, and finally freeze-dried in vacuo. The fluffy yellow polymer thus obtained was soluble in methane sulfonic acid, exhibiting an inherent viscosity in that solvent of 0.4 dl/g (0.35 g/dl).

Calc'd For $(C_{14}H_8N_4)_n$: C,72.40; H,3.47; N,24.12. Found: C,71.05; H,3.13; N,22.81.

EXAMPLE VII

2-[p-Carbophenoxphenyl]5,6-diaminobenzimidazole

To 25 ml of pyridine was added under nitrogen 2.5 g (5.2 mmole) of 2-[p-carbophenoxyphenyl]-5,6-diaminobenzimidazole dihydrochloride prepared by the above procedure. The dark solution was stirred at room temperature for ½ hour and then poured into 1 liter of ice water, liberating the bright yellow free amine. The yellow diamine thus formed was immediately filtered by suction, air-dried, and then recrystallized from methanol-water, yielding 1.2 g (68%) of 2-[p-carbophenoxyphenyl]-5,6-diaminobenzimidazole as a yellow powder, m.p. 237° C.

Calc'd for $C_{20}H_{16}N_4O_2$: C,69.76; H,4.68; N,16.27; O,9.29. Found: C,69.13; H,4.52; H,15.88.

Mol wt (Calculated) = 344.38
Mol wt (Mass spectrum) = 344.

EXAMPLE VIII

Polymerization of 2-[p-Carbophenoxyphenyl]-5,6-Diaminobenzimidazole

A polymerization flask equipped with nitrogen inlet and outlet tubes and mechanical stirrer was thoroughly flamed and purged with nitrogen. To this was added a mixture containing 5.0 g (14.5 mmole) of 2-[p-carbophenoxyphenyl]-5,6-diaminobenzimidazole and 25 g of diphenyl sulfone. The reaction flask was then slowly heated to 250° C and maintained at that temperature for 6 hours. During this time, phenol sublimed from the reaction mixture, and a precipitate formed. The flask was cooled to 125° C and the polymer suspension poured into 500 ml of methanol. The polymer thus precipitated was collected on a filter frit, washed several times with small portions of methanol, and dried. Reprecipitation from methane sulfonic acid into methanol, followed by successive washings with 5% ammonium hydroxide, methanol and benzene, yielded 2.9 g of benzimidazole polymer as a dark tan powder, exhibiting an inherent viscosity of 1.1 dl/g in methane sulfonic acid (0.35 g/dl).

Calc'd for $(C_{14}H_8N_4)_n$: C,72.40; H,3.47; N,24.12. Found: C,70.93; H,3.40; N,22.44.

EXAMPLE IX

2-[p-Carbophenoxyphenyl]-5,6-bis(p-toluenesulfonamide)benzimidazole

To a solution containing 8.7 g (33.6mmole) of p-chlorocarbonylphenylbenzoate dissolved in 50 ml of dichlorobenzene was added 5 g (11.2 mmole) of 1,2-diamino-4,5-bis(p-toluenesulfonamido)benzene. The resulting mixture was heated to reflux under nitrogen (frothing), and was maintained at that temperature for 2 hours. The solution was then distilled to half of the original volume, and heptane was added to precipitate the yellow product. The crude product was filtered, washed with several portions of hexane, and air-dried. The material thus obtained was reprecipitated three times from THF solution using hexane. Recrystallization from methanol afforded 5.6 g (77%) of 2-[p-carbophenoxyphenyl]-5,6-bis(p-toluenesulfonamido)-benzimidazole as an amorphous yellow powder.

Calc'd for $C_{34}H_{26}N_4O_6S_2$: C,62.76; H,4.02; N,8.61; O,14.75; S,9.85. Found: C,62.34; H,3.87; N,8.15.

EXAMPLE X

Polymerization of 2-[p-Carbophenoxyphenyl]-5,6-bis(p-toluenesulfonamido)benzimidazole A polymerization flask equipped with nitrogen inlet and outlet tubes and mechanical stirrer was thoroughly flamed and purged with nitrogen. To this was added 50 g of polyphosphoric acid, and the viscous material was stirred at 150° C under nitrogen for 3 hours. The flask was then cooled in ice, opened, and 2.0 g (3.06 mmole) of 2-[p-carbophenoxyphenyl]-5,6-bis(p-toluenesulfonamido)benzimidazole was added. The flask was closed, and the resulting suspension stirred at 90° for 8 hours under nitrogen to hydrolyze the tosylate and ester groups, liberating the diamino-acid monomer. At that point, a clear, brown solution remained. The temperature of the heating bath was then slowly raised over a period of 3 hours to a maximum of 200° C, and was maintained at that level for 8 hours. The dark brown polymer solution was precipitated into a large volume of methanol. Workup as in the preceding examples afforded a brownish-yellow polymer which exhibited an inherent viscosity of 0.2 dl/g in methanesulfonic acid (0.35 g/dl).

Calc'd for $(C_{14}H_8N_4)_n$: C,72.40; H,3.47; N,24.12. Found: C,71.20; H,4.01; N,23.00.

From the foregoing it is seen that the monomers of this invention can be polymerized to a high molecular weight, all para-oriented polybenzimidazole. Because of its structure, the polybenzimidazole is particularly suitable for use in fabricating composites having improved physical properties. The polymer can also be used in the preparation of protective coatings, films and fibers.

As will be evident to those skilled in the art, modifications of the present invention can be made in view of the foregoing disclosure without departing from the spirit or scope of the invention.

We claim:

1. A substituted phenyl-benzimidazo compound having the following structural formula:

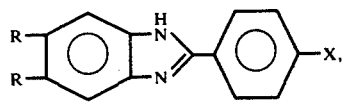

wherein R is $-NHSO_2R'$ and X is

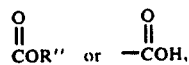

with R' being tolyl and with R" being phenyl.

2. The compound according to claim 1 in which R' is tolyl and X is

3. A substituted phenyl-benzimidazo compound having the following structural formula:

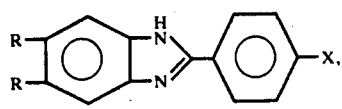

wherein R is $-NHSO_2R'$ and X is

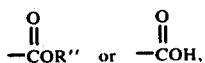

with R' being phenyl, tolyl, xylyl, naphthyl, diphenyl, methylnaphthyl, benzyl, chlorophenyl, bromophenyl, iodophenyl, fluorophenyl, chloronaphthyl, chlorodiphenyl, methyl, ethyl, propyl, amyl, octyl, decyl, dodecyl, octadecyl, cyclohexyl, cycloheptyl, methylcyclohexyl, or ethylcycloheptyl, and with R" being methyl, ethyl, propyl, butyl, cyclopropyl, cyclopentyl, cyclohexyl, cycloheptyl, tolyl, xylyl, phenyl, biphenyl, or naphthyl.

* * * * *